(12) United States Patent
Okajima et al.

(10) Patent No.: US 10,357,618 B2
(45) Date of Patent: Jul. 23, 2019

(54) INJECTION-NEEDLE COVER

(71) Applicants: TAKEDA PHARMACEUTICAL COMPANY LIMITED, Osaka-shi, Osaka (JP); YOSHINO KOGYOSHO CO., LTD., Tokyo (JP); ARTE CORPORATION, Tokyo (JP)

(72) Inventors: Kiyoshi Okajima, Takahagi (JP); Yuki Imanishi, Ibaraki (JP); Naoki Asakawa, Osaka (JP); Nobuo Tanaka, Osaka (JP); Yusuke Chuma, Osaka (JP)

(73) Assignees: TAKEDA PHARMACEUTICAL COMPANY LIMITED, Osaka-Shi (JP); YOSHINO KOGYOSHO CO., LTD., Tokyo (JP); ARTE CORPORATION, Tokyo (JP)

( * ) Notice: Subject to any disclaimer, the term of this patent is extended or adjusted under 35 U.S.C. 154(b) by 58 days.

(21) Appl. No.: 15/535,186

(22) PCT Filed: Dec. 17, 2015

(86) PCT No.: PCT/JP2015/085393
§ 371 (c)(1),
(2) Date: Jun. 12, 2017

(87) PCT Pub. No.: WO2016/098861
PCT Pub. Date: Jun. 23, 2016

(65) Prior Publication Data
US 2017/0326307 A1 Nov. 16, 2017

(30) Foreign Application Priority Data
Dec. 19, 2014 (JP) ................................. 2014-257759

(51) Int. Cl.
*A61M 5/32* (2006.01)

(52) U.S. Cl.
CPC ............ *A61M 5/3204* (2013.01); *A61M 5/32* (2013.01); *A61M 5/3216* (2013.01); *A61M 5/3245* (2013.01); *A61M 5/3275* (2013.01)

(58) Field of Classification Search
CPC .... A61M 5/32; A61M 5/3204; A61M 5/3216; A61M 5/3245; A61M 5/3275
See application file for complete search history.

(56) References Cited

U.S. PATENT DOCUMENTS

| | | |
|---|---|---|
| 5,232,454 A | 8/1993 | Hollister |
| 5,348,544 A | 9/1994 | Sweeney et al. |

(Continued)

FOREIGN PATENT DOCUMENTS

| | | |
|---|---|---|
| JP | 4-244167 | 9/1992 |
| JP | 7-250898 | 10/1995 |

(Continued)

OTHER PUBLICATIONS

International Search Report, dated Feb. 23, 2016 (Feb. 23, 2016), 4 pages.
European Search Report dated Jun. 19, 2018, 8 pages.

*Primary Examiner* — Imani N Hayman
(74) *Attorney, Agent, or Firm* — Rankin, Hill & Clark LLP

(57) ABSTRACT

A injection-needle cover includes an injection needle enclosure portion, which has paired base-side wall portions, a cylinder portion, paired tip-end-side wall portions, an injection needle contact portion, a hook portion, and a needle tip end fixing portion. The injection needle contact portion is disposed at a position in a base-side axial space, which is a boundary between the base-side axial space and an intra-cylinder space. The injection needle contact portion has a force receiving portion and a connecting portion. The force receiving portion receives a force from the injection needle when the force receiving portion comes in contact with the (Continued)

injection needle. The force receiving portion has an easy sliding portion, which is disposed in an area adjacent to an injection needle, and slides more easily along the injection needle than a case where an edge slides along the injection needle.

8 Claims, 14 Drawing Sheets

(56) References Cited

U.S. PATENT DOCUMENTS

| | | |
|---|---|---|
| 2001/0021827 A1 | 9/2001 | Ferguson et al. |
| 2001/0039401 A1 | 11/2001 | Ferguson et al. |
| 2003/0004465 A1 | 1/2003 | Ferguson et al. |
| 2003/0191438 A1 | 10/2003 | Ferguson et al. |
| 2009/0287149 A1 | 11/2009 | Koh |
| 2010/0280413 A1 | 11/2010 | Ferguson et al. |

FOREIGN PATENT DOCUMENTS

| | | |
|---|---|---|
| JP | 2001-515767 | 9/2001 |
| JP | 2003-514596 | 4/2003 |
| JP | 2005-521537 | 7/2005 |
| JP | 2005-528188 | 9/2005 |
| JP | 2009-535105 | 10/2009 |
| JP | 2010-531675 | 9/2010 |
| WO | 99/12592 | 3/1999 |
| WO | 01/32241 A1 | 5/2001 |
| WO | 02/070056 A1 | 9/2002 |
| WO | 2007/127345 A2 | 11/2007 |

INJECTION-NEEDLE COVER

TECHNICAL FIELD

The present invention relates to an injection-needle cover.

BACKGROUND OF THE INVENTION

Patent Document 1 discloses a safe injection-needle cover which is extendable with respect to an injection needle. The injection-needle cover is formed by a plurality of rigid segments serially connected by a plurality of intersegment hinges. The rigid segments are disposed around the injection needle, folded upon each other during a medical procedure, and extended at the end of the medical procedure. The extended injection-needle cover protectively sheathes the injection needle.

PRIOR ART DOCUMENT

Patent Document

Patent Document 1: Japanese Translation of PCT Publication No. 2001-515767

SUMMARY OF THE INVENTION

Problem to be Solved by the Invention

However, the injection-needle cover disclosed in Patent Document 1 fails to be extended smoothly depending on size of the needle. If the injection-needle cover cannot be extended smoothly, a health practitioner is forced to handle this trouble. If it takes time to handle the trouble, provision of care for a patient may be delayed. The delay in the provision of the care for the patient may be seriously detrimental to the patient in some cases.

If the injection-needle cover disclosed in Patent Document 1 cannot be extended smoothly and the health practitioner tries to extend the injection-needle cover, it may cause an accident in some cases. As an example of the accident, the health practitioner may accidentally stick himself/herself with the injection needle. Such an accident may cause infection of the health practitioner in some cases.

The present invention has been made to solve the problem. It is an object of the invention to provide an injection-needle cover which can be extended easily and smoothly.

Solutions to the Problem

As a result of hard studies on the problem, the present inventors have found that specific operation of the injection-needle cover obstructs following operation and have achieved the invention. The invention is as follows.

An injection-needle cover according to a first aspect of the present invention includes:

a base portion which is fixed to an injection needle protruding face of a syringe, having a cylinder and an injection needle protruding from the cylinder, so as to enclose the injection needle, the injection needle protruding face being a face of the syringe from which the injection needle is protruding from the cylinder;

a base hinge which is a hinge provided to the base portion;

a connected portion fitting space forming portion which is connected to the base portion by the base hinge so as to turn about a base axis orthogonal to a central axis of the injection needle and which forms a space where a portion of the injection needle connected to the cylinder is to become fitted;

a connecting hinge which is a hinge provided to the connected portion fitting space forming portion; and an injection needle enclosure portion which is connected to the connected portion fitting space forming portion by the connecting hinge so as to turn about a connection axis parallel to the base axis, the injection needle enclosure portion including paired base-side wall portions forming a base-side axial space where a portion of the injection needle is to become fitted, a cylinder portion which is continuous from the paired base-side wall portions and which forms an intra-cylinder space communicating with the base-side axial space, paired tip-end-side wall portions which are continuous from the cylinder portion, which form a tip-end-side axial space where a tip end portion of the injection needle is to become fitted, so that the tip-end-side axial space communicates with the intra-cylinder space, and which are disposed on the opposite side of the cylinder portion from the paired base-side wall portions so that the base-side axial space and the tip-end-side axial space are aligned with each other, and an injection needle contact portion disposed at such a position in one of the base-side axial space and the intra-cylinder space as to come in contact with the injection needle when the base hinge opens, wherein the injection needle contact portion has a force receiving portion which receives a force from the injection needle when the force receiving portion comes in contact with the injection needle and a connecting portion which connects the paired base-side wall portions or the cylinder portion to the force receiving portion and the force receiving portion has an easy sliding portion which is disposed in an area adjacent to an injection needle and which slides along the injection needle more easily than a case where an edge having an equal coefficient of static friction to a surface of the connecting portion and crossing the injection needle slides, the area being closer to an area on a side of the tip-end-side axial space than a portion, which faces the injection needle after the injection needle becomes fitted in the base-side axial space and the tip-end-side axial space.

In addition to the structures according to the first aspect, in the injection-needle cover according to a second aspect of the invention, the easy sliding portion has an injection needle contact zone extending along a direction of movement of the easy sliding portion in opening of the connecting hinge.

In addition to the structures according to the second aspect, in the injection-needle cover according to a third aspect of the invention, the injection needle contact zone is provided with a curved face extending from one end to the other end of the injection needle contact zone in the direction of the movement of the easy sliding portion in the opening of the connecting hinge.

In addition to the structures according to the first to third aspects, in the injection-needle cover according to a fourth aspect of the invention, the connected portion fitting space forming portion has a moment receiving portion 44 for receiving moment about the base axis as a turning center.

In addition to the structures according to the first to fourth aspects, in the injection-needle cover according to a fifth aspect of the invention, the connecting portion has a bottom plate portion which is disposed in the base-side axial space to be adjacent to a boundary between the base-side axial space and the intra-cylinder space and opposite ends of which are connected to the base-side wall portions and a structural body portion protruding from an end portion of the bottom plate portion facing the intra-cylinder space toward the base-side axial space and a curved face is provided to a portion of the bottom plate portion extending from the opposite face from a face facing the base-side axial space to the end portion.

In addition to the structures according to the first to fifth aspects, in the injection-needle cover according to a sixth aspect of the invention, the connecting portion has a flexible body portion which bends more in a direction from the tip-end-side axial space toward the base-side axial space than in a direction orthogonal to the direction from the tip-end-side axial space toward the base-side axial space when the force receiving portion receives the force from the injection needle.

In addition to the structures according to the sixth aspect, in the injection-needle cover according to a seventh aspect of the invention, the flexible body portion has a plate-shaped portion disposed to be orthogonal to a bending direction which is the direction from the tip-end-side axial space toward the base-side axial space.

In addition to the structures according to the seventh aspect, in the injection-needle cover according to an eighth aspect of the invention, the plate-shaped portion faces one of the paired base-side wall portions with a clearance left therebetween and the force receiving portion faces the one of the paired base-side wall portions, which the plate-shaped portion faces with the clearance left therebetween, with a clearance left therebetween.

In addition to the structures according to the eighth aspect, in the injection-needle cover according to a ninth aspect of the invention, the injection needle enclosure portion further has a hook portion which is protruding into the base-side axial space and which hooks the injection needle when the injection needle becomes fitted in the base-side axial space and the tip-end-side axial space, the hook portion has a columnar portion disposed along the paired base-side wall portions in the base-side axial space, a detachment preventing portion protruding from the columnar portion toward one of the paired base-side wall portions, and an inclined face disposed from a tip end portion of the columnar portion to a tip end portion of the detachment preventing portion and inclined with respect to a direction along the paired base-side wall portions, and the plate-shaped portion is connected to the base-side wall portion, toward which the detachment preventing portion is protruding, and faces the different base-side wall portion from the base-side wall portion, toward which the detachment preventing portion is protruding, with the clearance left therebetween.

In addition to the structures according to the sixth to ninth aspects, in the injection-needle cover according to a tenth aspect of the invention, the flexible body portion has a less deformable portion extending in a direction crossing the base-side wall portions and a more deformable portion extending along the less deformable portion and more deformable than the less deformable portion.

In addition to the structures according to the tenth aspect, in the injection-needle cover according to an eleventh aspect of the invention, the more deformable portion is provided with a slit extending along the less deformable portion.

Effect of the Invention

According to the aspects of the present invention, it is possible to provide an injection-needle cover which can be extended easily and smoothly.

MODE FOR CARRYING OUT THE INVENTION

With reference to the drawings, an embodiment of the present invention will be described. In the following description, the same parts will be provided with the same reference signs and have the same names and functions and therefore will not be described in detail repeatedly.

[Description of Attached State of Injection-Needle Cover]

Figure 1:
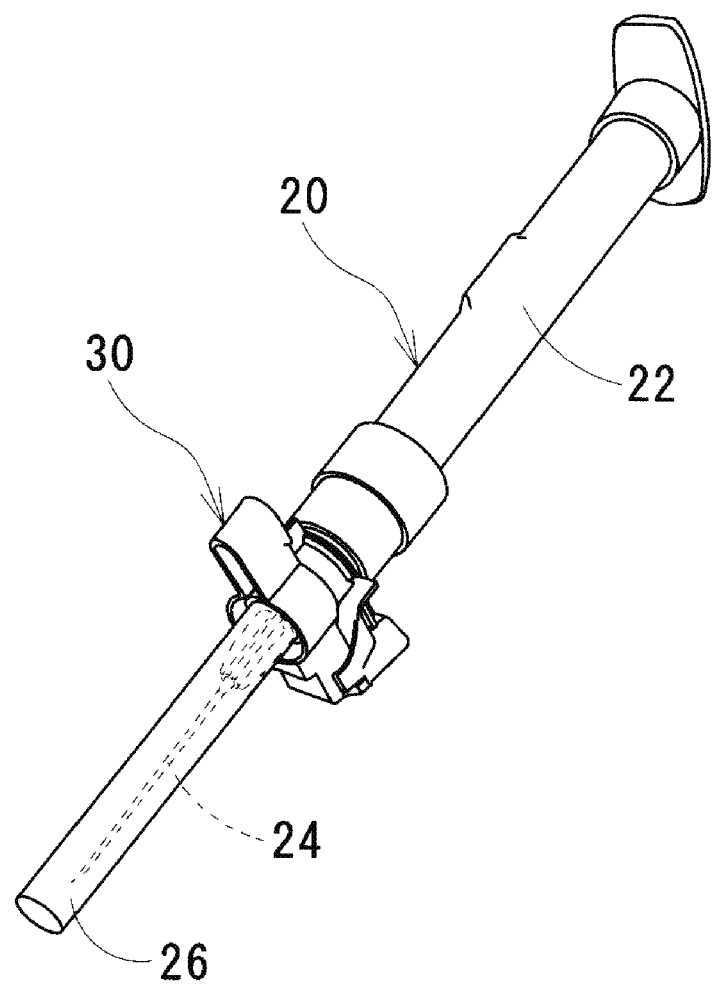
FIG. 1 is a view showing an attached state of an injection-needle cover according to an embodiment of the present invention to a syringe.
Figure 2:
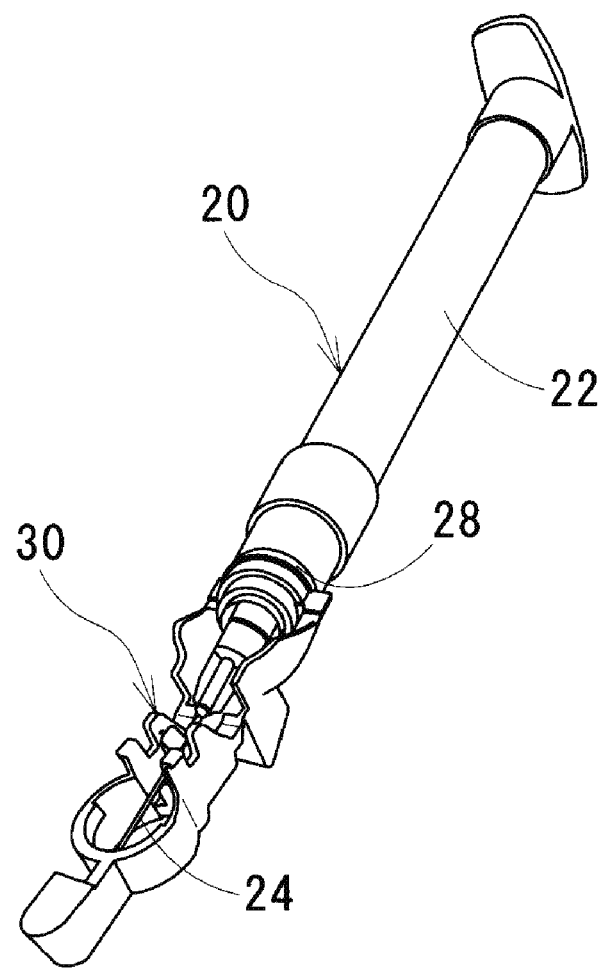
FIG. 2 is a view showing a state of the injection-needle cover according to the embodiment of the invention enclosing an injection needle.

FIG. 1 is a view showing an attached state of an injection-needle cover 30 according to the embodiment to a syringe 20. As shown in FIG. 1, the injection-needle cover 30 according to the embodiment is attached to the known syringe 20. Before use of the syringe 20, an injection needle 24 is covered with a cylindrical cover 26. The injection-needle cover 30 according to the embodiment encloses the injection needle 24 of the syringe 20 after the use of the syringe 20. FIG. 2 is a view showing a state of the injection-needle cover 30 according to the embodiment enclosing the injection needle 24. The cylindrical cover 26 is removed to use the syringe 20. In the embodiment, a known cylinder to which the known injection needle 24 is attached is referred to as a cylinder 22. In the embodiment, the injection needle 24 and the cylinder 22 to which the injection needle 24 is attached are collectively referred to as the syringe 20.

[Description of Structure of Injection-Needle Cover]

Figure 3:
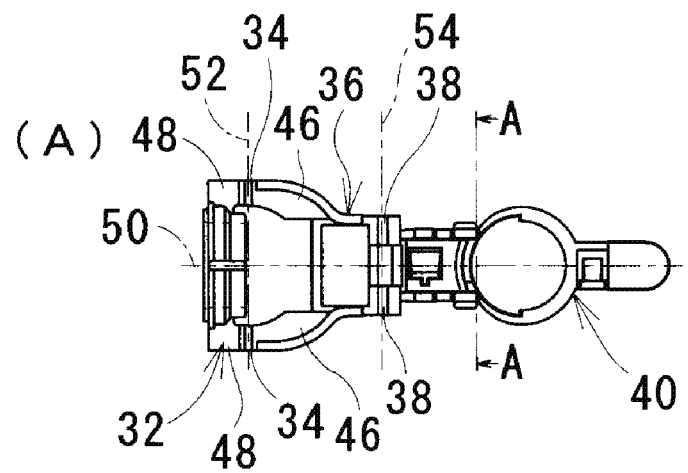
FIGS. 3(A) to 3(C) are external views of the injection-needle cover according to the embodiment of the invention.
Figure 3:
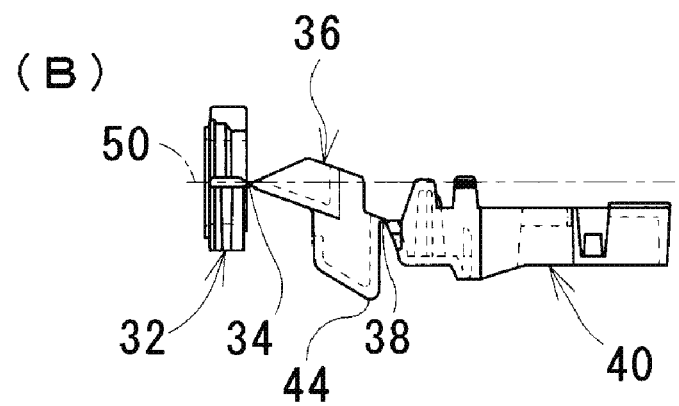
Figure 3:
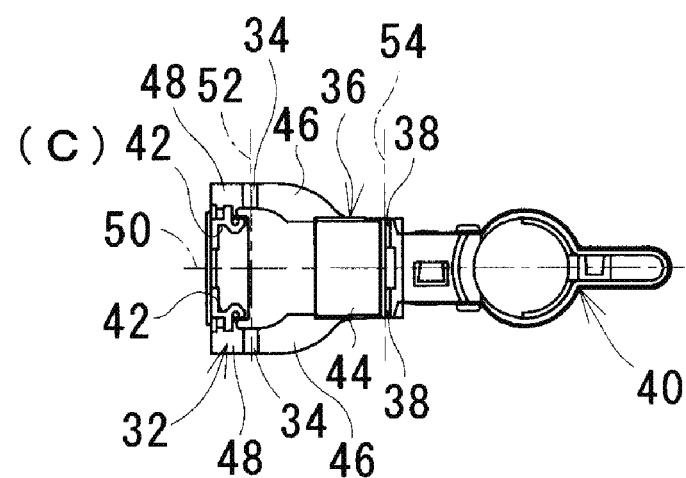

FIGS. 3(A) to 3(C) are external views of the injection-needle cover 30 according to the embodiment of the invention. FIG. 3(A) is a plan view of the injection-needle cover 30 according to the embodiment. FIG. 3(B) is a front view of the injection-needle cover 30 according to the embodiment. FIG. 3(C) is a bottom view of the injection-needle cover 30 according to the embodiment. The injection-needle cover 30 according to the embodiment will be described based on FIGS. 3(A) to 3(C). The injection-needle cover 30 according to the embodiment is made of synthetic resin. The injection-needle cover 30 according to the embodiment includes a base portion 32, paired base hinges 34, a connected portion fitting space forming portion 36, paired connecting hinges 38, and an injection needle enclosure portion 40. In the embodiment, these parts are integrated with each other.

In the embodiment, the base portion 32 is in an annular shape from opposite ends of which ribs 48 are protruding. In the embodiment, a smooth side face of the base portion 32 facing an injection needle protruding face 28 of the cylinder 22 and the injection needle protruding face 28 are integrated with each other by welding. In the embodiment, the welding is achieved by rotating the former while pushing the former against the latter. In this way, the base portion 32 is fixed to the injection needle protruding face 28. The injection needle protruding face 28 is a smooth face of the cylinder 22 from which the injection needle 24 is protruding. The base portion 32 is fixed so as to enclose the injection needle 24. As shown in FIG. 3(C), the base portion 32 includes retaining portions 42 as well. Fixing lugs 90 (described later) get caught on the retaining portions 42.

The base hinges 34 are hinges provided to the base portion 32. In the embodiment, the base hinges 34 are continuous with the ribs 48 at opposite ends of the base portion 32.

The connected portion fitting space forming portion 36 is connected to the base portion 32 by the base hinges 34. In this way, the connected portion fitting space forming portion 36 turns about a base axis 52. The base axis 52 passes through the base hinges 34 and is orthogonal to a central axis 50 of the injection-needle cover 30 (the central axis 50 passes through a center of the base portion 32). The connected portion fitting space forming portion 36 forms a space. In the space, a portion of the injection needle 24 connected to the cylinder 22 is to become fitted (in the embodiment, not only a portion formed by a metal tube but also the connected portion is a part of the injection needle 24). The connected portion fitting space forming portion 36 includes paired arm portions 46 and a moment receiving portion 44. The arm portions 46 connect the base hinges 34 and the moment receiving portion 44. The paired arm portions 46 are respectively connected to the different base hinges 34. The moment receiving portion 44 receives moment about the base axis 52 as a turning center.

The connecting hinges 38 are hinges provided to the connected portion fitting space forming portion 36 with the moment receiving portion 44 interposed therebetween.

The injection needle enclosure portion 40 is connected to the connected portion fitting space forming portion 36 by the paired connecting hinges 38. The injection needle enclosure portion 40 turns about a connection axis 54. The connection axis 54 passes through the connecting hinges 38 and is parallel to the base axis 52.

Figure 4:
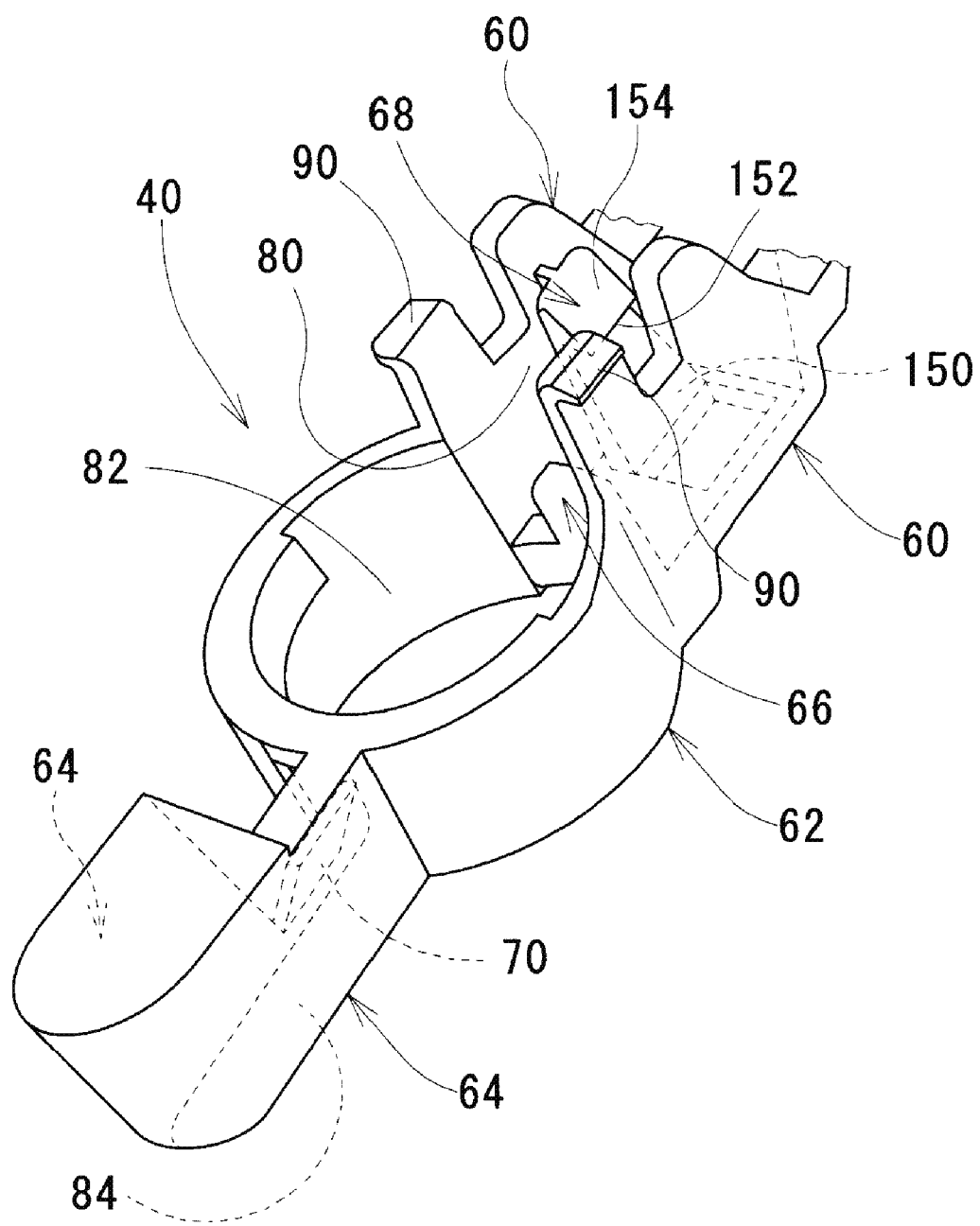
FIG. 4 is a perspective view of an injection needle enclosure portion according to the embodiment of the invention.

FIG. 4 is a perspective view of an injection needle enclosure portion 40 according to the embodiment of the invention. The injection needle enclosure portion 40 according to the embodiment will be described based on FIG. 4. The injection needle enclosure portion 40 according to the embodiment includes paired base-side wall portions 60, a cylinder portion 62, paired tip-end-side wall portions 64, an injection needle contact portion 66, a hook portion 68, and a needle tip end fixing portion 70.

The paired base-side wall portions 60 are disposed to face each other. A space between the paired base-side wall portions 60 is a base-side axial space 80. In this way, the paired base-side wall portions 60 form the base-side axial space 80. In the base-side axial space 80, a part of the injection needle 24 is to become fitted. Each of the base-side wall portions 60 has the fixing lug 90. The fixing lugs 90 pass through the space formed by the connected portion fitting space forming portion 36 and get caught on the retaining portions 42 of the base portion 32. As a result, the injection-needle cover 30 according to the embodiment takes the form shown in FIG. 1.

The cylinder portion 62 is continuous with the paired base-side wall portions 60. The cylinder portion 62 forms an intra-cylinder space 82. The space surrounded with an inner peripheral face of the cylinder portion 62 is the intra-cylinder space 82. As is clear from FIG. 4, the intra-cylinder space 82 communicates with the base-side axial space 80 through a notch formed in the cylinder portion 62.

The paired tip-end-side wall portions 64 are disposed to face each other. The paired tip-end-side wall portions 64 are continuous with the cylinder portion 62. A space between the paired tip-end-side wall portions 64 is a tip-end-side axial space 84. In this way, the paired tip-end-side wall portions 64 form the tip-end-side axial space 84. A tip end portion of the injection needle 24 is to become fitted in the tip-end-side axial space 84. The tip-end-side axial space 84 communicates with the intra-cylinder space 82 through a notch formed in the cylinder portion 62. The paired tip-end-side wall portions 64 are disposed on the opposite side of the cylinder portion 62 from the paired base-side wall portions 60. The paired tip-end-side wall portions 64 are disposed so that the base-side axial space 80 and the tip-end-side axial space 84 are aligned with each other.

In the embodiment, the injection needle contact portion 66 is disposed at a position in the base-side axial space 80 which is a boundary between the base-side axial space 80 and the intra-cylinder space 82.

The hook portion 68 is protruding into the base-side axial space 80. The hook portion 68 according to the embodiment includes a columnar portion 150, a detachment preventing portion 152, and an inclined face 154. The columnar portion 150 is disposed in the base-side axial space 80. The columnar portion 150 is provided along the paired base-side wall portions 60. The detachment preventing portion 152 is protruding from the columnar portion 150 toward one of the paired base-side wall portions 60. The inclined face 154 is disposed from a tip end portion of the columnar portion 150 to a tip end portion of the detachment preventing portion 152. The inclined face 154 is inclined with respect to a direction along the paired base-side wall portions 60.

The needle tip end fixing portion 70 is protruding from one of the tip-end-side wall portions 64 into the tip-end-side axial space 84. The hook portion 68 and the needle tip end fixing portion 70 catch the injection needle 24 when the injection needle 24 becomes fitted into the base-side axial space 80 and the tip-end-side axial space 84.

Figure 5:
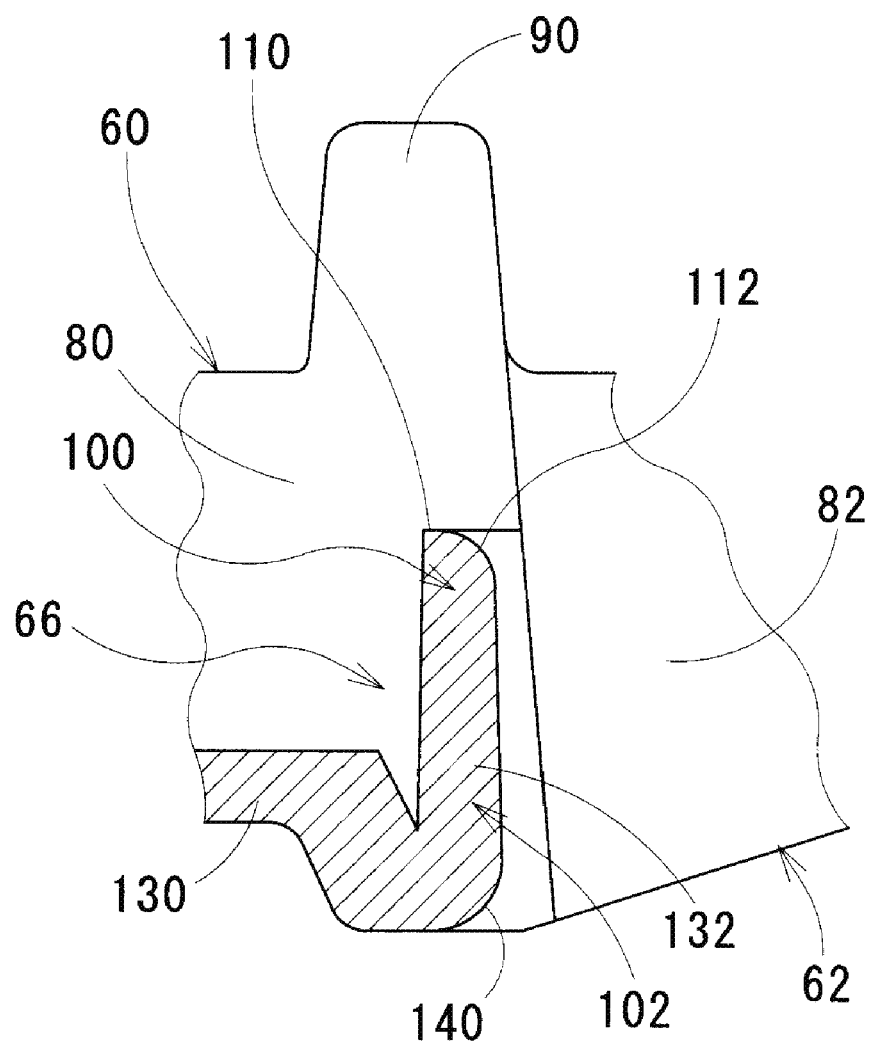
FIG. 5 is a sectional view of an injection needle contact portion according to the embodiment of the invention.

FIG. 5 is a sectional view of an injection needle contact portion 66 according to the embodiment. FIG. 5 shows a section of the injection needle contact portion 66 along the central axis 50 of the injection-needle cover 30. The injection needle contact portion 66 according to the embodiment will be described based on FIG. 5. The injection needle contact portion 66 according to the embodiment includes a force receiving portion 100 and a connecting portion 102. In the embodiment, the force receiving portion 100 and the connecting portion 102 are integrated with each other.

The force receiving portion 100 receives a force from the injection needle 24 when the force receiving portion 100 comes in contact with the injection needle 24. The force receiving portion 100 includes an injection needle facing portion 110 and an easy sliding portion 112.

The injection needle facing portion 110 faces the injection needle 24 after the injection needle 24 becomes fitted in the base-side axial space 80 and the tip-end-side axial space 84. The easy sliding portion 112 is disposed in an area adjacent to the injection needle. In the embodiment, the area adjacent to the injection needle refers to an area of the force receiving portion 100 on a side closer to the intra-cylinder space 82 and the tip-end-side axial space 84 than the injection needle facing portion 110.

Figure 6:
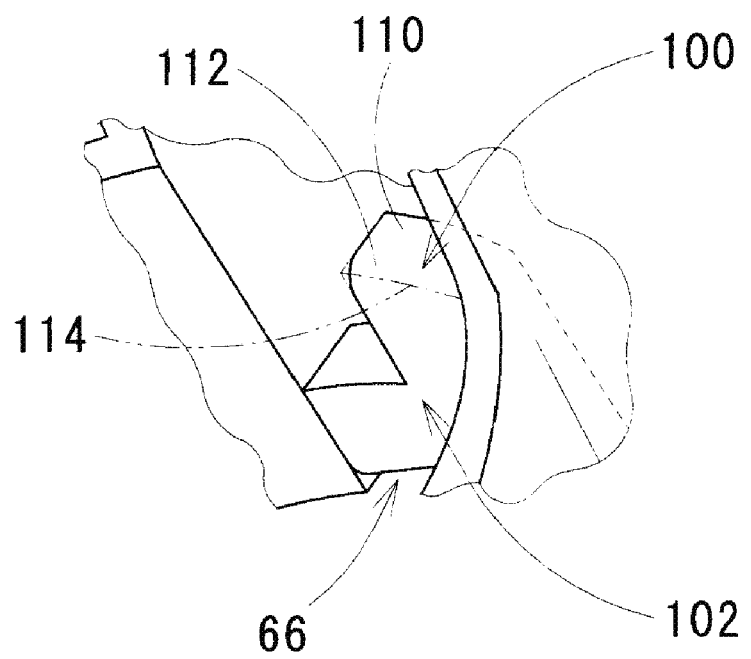
FIG. 6 is a perspective view of an easy sliding portion according to the embodiment of the invention.
Figure 7:
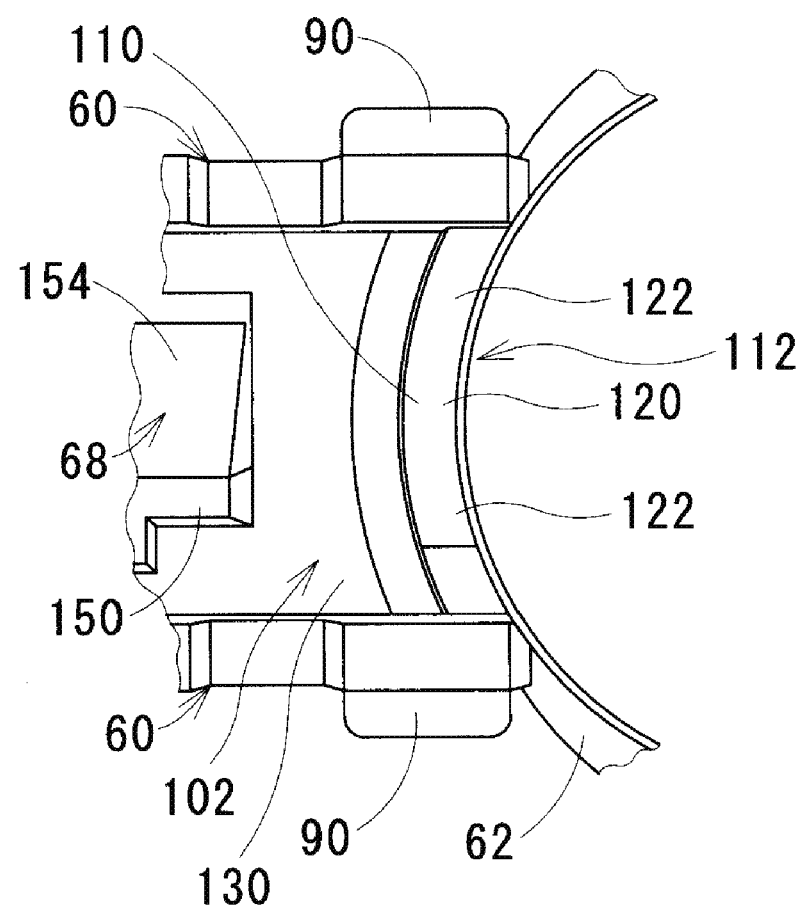
FIG. 7 is an enlarged view of FIG. 3(A).
Figure 8:
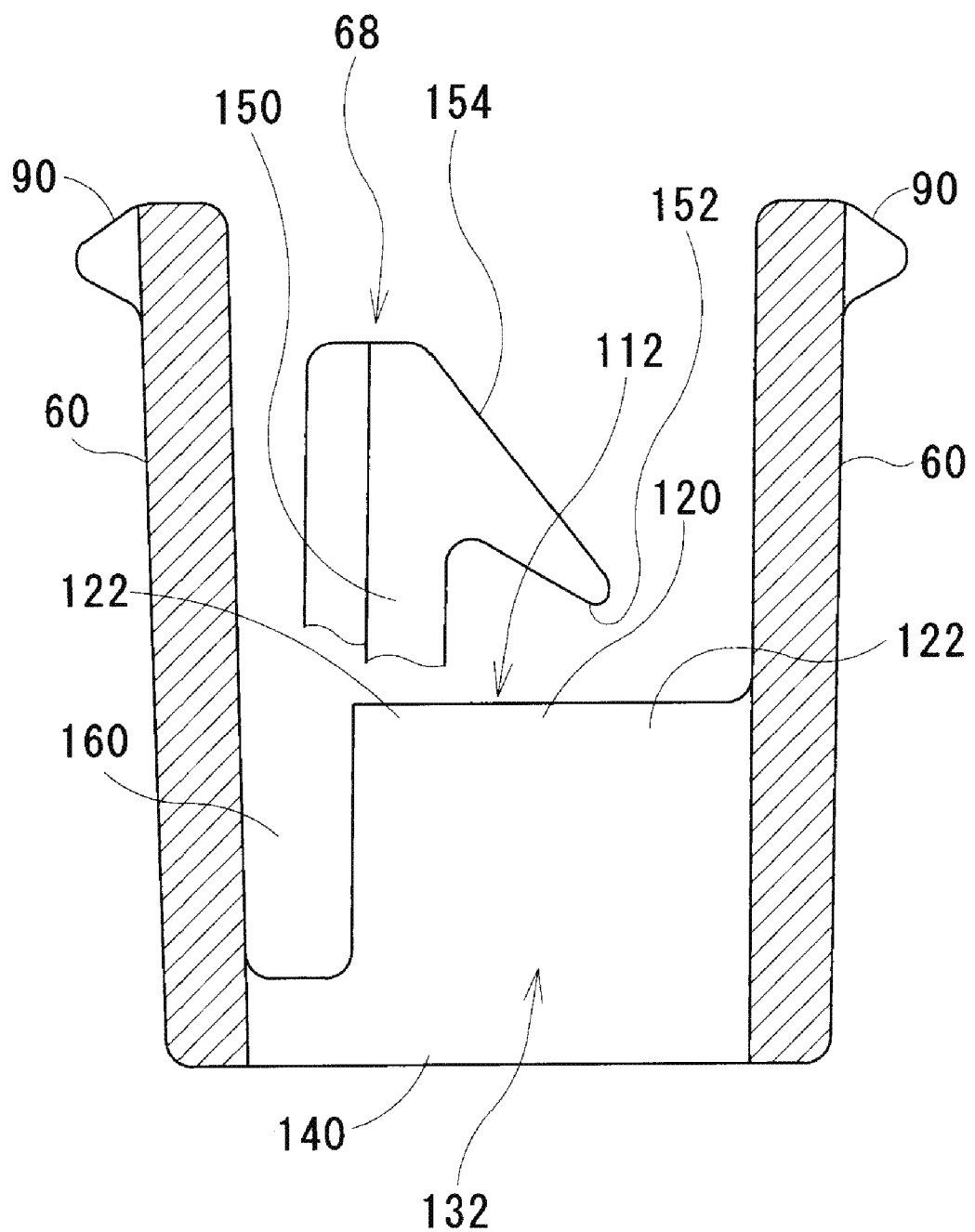
FIG. 8 is a sectional view taken along line A-A in FIG. 3(A).

FIG. 6 is a perspective view of the easy sliding portion 112 according to the embodiment. FIG. 7 is an enlarged view of an area around a boundary between the base-side axial space 80 and the intra-cylinder space 82 in FIG. 3(A). FIG. 8 is a sectional view taken along line A-A in FIG. 3(A). The easy sliding portion 112 according to the embodiment will be described based on FIGS. 6 to 8. The easy sliding portion 112 is a portion which slides more easily along the injection needle 24 than a case where an edge 114 having an equal coefficient of static friction to the connecting portion 102 and crossing the injection needle 24 slides along the injection needle 24. As shown in FIGS. 7 and 8, in the embodiment, the easy sliding portion 112 includes an injection needle contact zone 120 and paired injection needle position correcting zones 122.

The injection needle contact zone 120 is extending along a direction of movement of the easy sliding portion 112 in opening of the connecting hinges 38. This direction is a direction from the hook portion 68 toward the injection needle facing portion 110 in FIG. 7. In the embodiment, a curved face is provided throughout the injection needle contact zone 120. The curved face extends from one end to the other end of the injection needle contact zone 120 in the direction of the movement of the easy sliding portion 112 in the opening of the connecting hinges 38. In the embodiment, a radius of curvature of the curved face equals to a thickness of the injection needle contact portion 66 at a base of the force receiving portion 100 (a connection between the force receiving portion 100 and the connecting portion 102). Needless to say, the radius of curvature may be larger or smaller than the thickness of the injection needle contact portion 66. The paired injection needle position correcting zones 122 are disposed to sandwich the injection needle facing portion 110. In the embodiment, the injection needle position correcting zones 122 are extending in a direction along the inner peripheral face of the cylinder portion 62 as well as in the direction of the movement of the easy sliding portion 112 in the opening of the connecting hinges 38. In this way, when a metal tube portion of the injection needle 24 bends, the injection needle position correcting zones 122 can correct the bend. In the embodiment, curved faces are respectively provided throughout the injection needle position correcting zones 122. In the embodiment, the curved faces and the curved face provided throughout the injection needle contact zone 120 are integrated with each other. In this way, it is possible to smoothly correct the bend when the metal tube portion of the injection needle 24 bends.

In the embodiment, the connecting portion 102 connects the paired base-side wall portions 60 and the force receiving portion 100. The connecting portion 102 according to the embodiment will be described based on FIGS. 5, 7, and 8. In the embodiment, the connecting portion 102 includes a bottom plate portion 130 and a plate-shaped portion 132.

In the embodiment, the bottom plate portion 130 is disposed in the base-side axial space 80 to extend from a boundary between the base-side axial space 80 and the intra-cylinder space 82 to a vicinity of the connecting hinges 38. As shown in FIG. 7, opposite ends of the bottom plate portion 130 are connected to the base-side wall portions 60. As shown in FIG. 5, the bottom plate portion 130 is provided with a bottom curved face 140. In the embodiment, one end of the bottom curved face 140 is positioned on a face of the bottom plate portion 130 facing an outside of the injection-needle cover 30 (i.e., a face opposite from a face facing the base-side axial space 80). The other end of the bottom curved face 140 faces the intra-cylinder space 82.

As shown in FIG. 5, the plate-shaped portion 132 is protruding from the end portion of the bottom plate portion 130 facing the intra-cylinder space 82 (end portion provided with the bottom curved face 140) toward the base-side axial space 80. The plate-shaped portion 132 is disposed to be orthogonal to a bending direction. In this case, the bending direction refers to a direction from the tip-end-side axial space 84 toward the base-side axial space 80. When the force receiving portion 100 receives a force from the injection needle 24, the plate-shaped portion 132 bends more in the direction from the tip-end-side axial space 84 toward the base-side axial space 80 than in the direction orthogonal to the direction from the tip-end-side axial space 84 toward the base-side axial space 80. An example of "the direction orthogonal to the direction from the tip-end-side axial space 84 toward the base-side axial space 80" is a direction from one of the paired base-side wall portions 60 toward the other. In the embodiment, the plate-shaped portion 132 is connected to the base-side wall portion 60 toward which the detachment preventing portion 152 of the hook portion 68 is protruding. As shown in FIG. 8, in the embodiment, the plate-shaped portion 132 faces the different base-side wall portion 60 from the base-side wall portion 60 toward which the detachment preventing portion 152 is protruding (the base-side wall portion 60 toward which the detachment preventing portion 152 is not protruding) with a clearance 160 left therebetween. In the embodiment, the force receiving portion 100 is disposed similarly. Therefore, the force receiving portion 100 faces the base-side wall portion 60, which the plate-shaped portion 132 faces with the clearance 160 left therebetween, with the clearance 160 therebetween. In the embodiment, the clearance 160 is 1.3 mm in width. The width of the clearance 160 is determined based on the following basis. In other words, a clearance between the paired base-side wall portions 60 is 5.8 mm. An outer diameter of the metal tube portion of the injection needle 24 is assumed to be between 0.65 mm and 0.50 mm inclusive. An assumed maximum value of the outer diameter of the metal tube portion of the injection needle 24 is 0.65 mm. If the width of the clearance 160 exceeds a half of the clearance between the paired base-side wall portions 60, the injection needle 24 may fall into the clearance 160. In order to avoid this, the width of the clearance 160 is preferably not greater than the half of the interval between the paired base-side wall portions 60. It is more preferable that the width of the clearance 160 is not greater than a value obtained by subtracting a half of the outer diameter of the injection needle 24 from the half of the interval between the paired base-side wall portions 60. The half of the interval between the paired base-side wall portions 60 is 5.8 mm÷2=2.9 mm. A half of the assumed maximum value of the outer diameter of the injection needle 24 is 0.65 mm÷2=0.325 mm. 2.9 mm−0.325 mm=2.575 mm. Based on this, a maximum value of the width of the clearance 160 is set to 2.575 mm. This corresponds to about 44.4% of the interval between the paired base-side wall portions 60. As a result, the width of the clearance 160 in the embodiment is 1.3 mm. Needless to say, the width of the clearance 160 may be different.

[Description of Method of Using]

Figure 9:
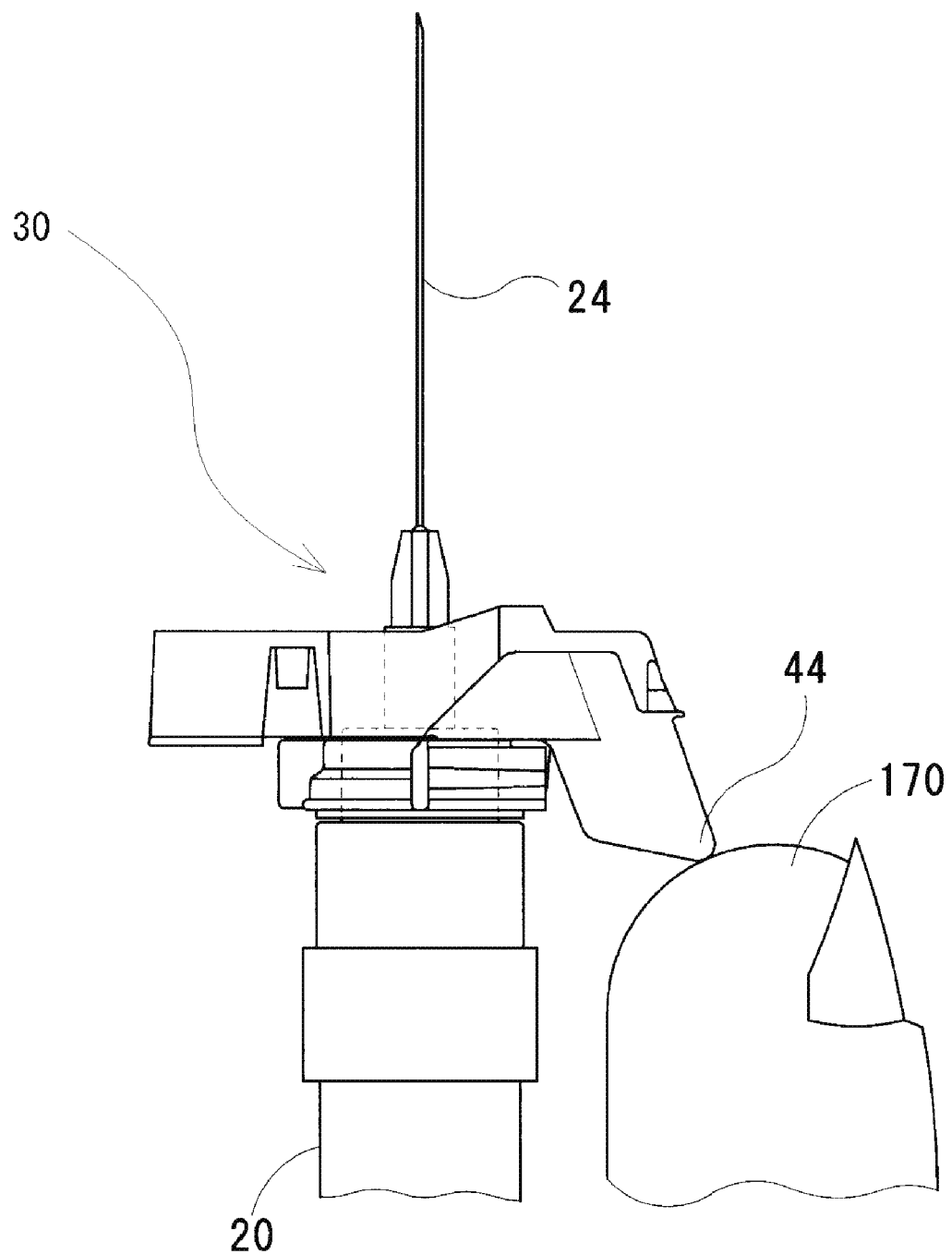
FIG. 9 is a view showing a state of the injection-needle cover according to the embodiment of the invention immediately before operation.
Figure 10:
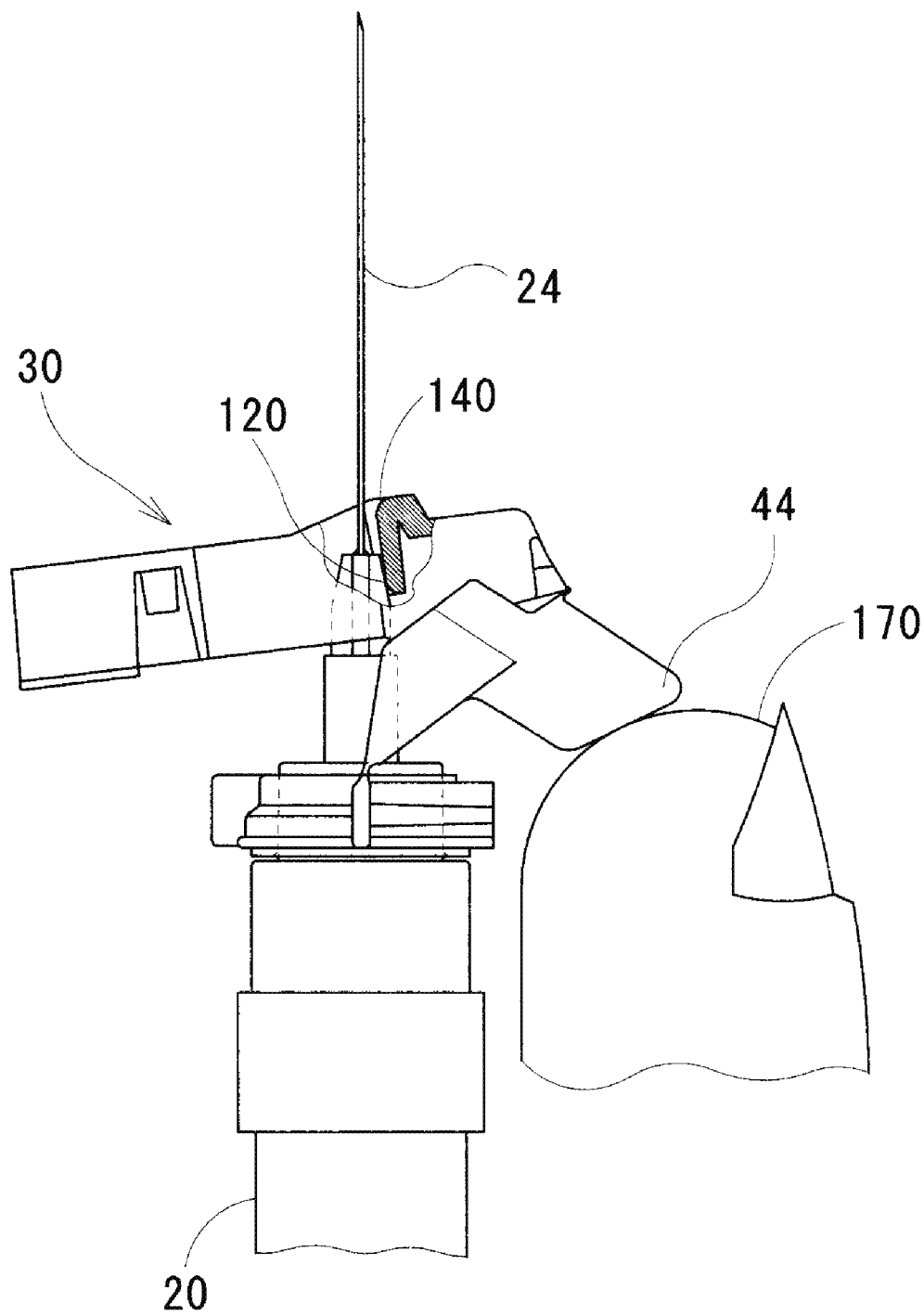
FIG. 10 is a view showing a state of the injection-needle cover according to the embodiment of the invention during the operation.
Figure 11:
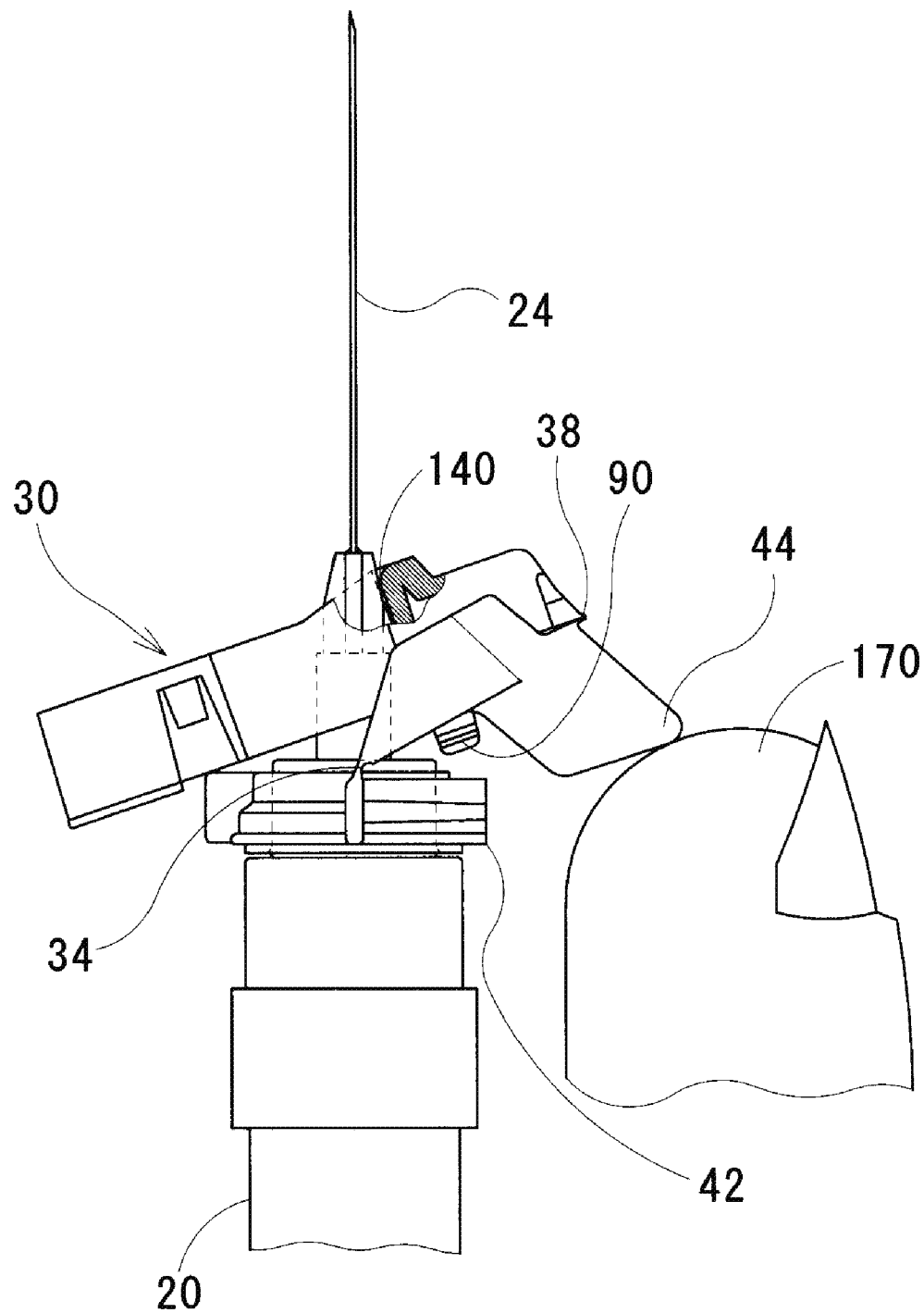
FIG. 11 is a view of the injection-needle cover according to the embodiment of the invention during the operation when connecting hinges open insufficiently.

FIG. 9 is a view showing a state of the injection-needle cover 30 according to the embodiment immediately before operation. FIG. 10 is a view showing a state of the injection-needle cover 30 according to the embodiment during operation. In this view, a part of the injection-needle cover 30 is cut away. FIG. 11 is a view of the injection-needle cover 30 according to the embodiment during the operation when the connecting hinges 38 insufficiently open. In this view, again, a part of the injection-needle cover 30 is cut away. The operation of the injection-needle cover 30 according to the embodiment will be described based on FIGS. 9 to 11.

First, a user takes the cylindrical cover 26 off the syringe 20 held in his/her hand. If the cylindrical cover 26 is taken off, the user uses the syringe 20. A method of using the syringe 20 is known. Therefore, the method will not be described here in detail.

After use of the syringe 20 is finished, the user holds the cylinder 22 of the syringe 20 in his/her hand. At this time, the user lightly touches the moment receiving portion 44 with his/her thumb 170 as shown in FIG. 9. When the user touches the moment receiving portion 44 with his/her thumb 170, the user pushes the moment receiving portion 44 in a direction parallel to the injection needle 24 with his/her thumb 170.

As the moment receiving portion 44 is pushed, the fixing lugs 90 caught on the retaining portions 42 are detached from the retaining portions 42. If the fixing lugs 90 are detached from the retaining portions 42, the folded injection-needle cover 30 is naturally extended by resilience of the base hinges 34 and resilience of the connecting hinges 38. The base hinges 34 and the connecting hinges 38 open. As a result, as shown in FIG. 10, the injection needle contact zone 120 of the easy sliding portion 112 comes in contact with a connected portion of the injection needle 24. At this time, the user keeps pushing the moment receiving portion 44 in the direction parallel to the injection needle 24 with his/her thumb 170. As the moment receiving portion 44 is kept pushed, the injection needle contact zone 120 moves along a base portion of the injection needle 24. A direction of movement of the injection needle contact zone 120 at this time is a direction of movement of the easy sliding portion 112 in opening of the connecting hinges 38.

If the connecting hinges 38 open insufficiently when the fixing lugs 90 are detached from the retaining portions 42, the bottom curved face 140 first comes in contact with the connected portion of the injection needle 24 as shown in FIG. 11. The bottom curved face 140 moves along the connected portion of the injection needle 24. The direction of movement of the injection needle contact zone 120 at this time is also the direction of the movement of the easy sliding portion 112 in the opening of the connecting hinges 38. Then, in place of the bottom curved face 140, the injection needle contact zone 120 of the easy sliding portion 112 comes in contact with the connected portion of the injection needle 24.

If the injection needle contact zone 120 of the easy sliding portion 112 moves along the connected portion of the injection needle 24 in this state, the injection needle 24 first becomes fitted in the tip-end-side axial space 84. The tip end portion of the injection needle 24 fitted in the tip-end-side axial space 84 gets caught on the needle tip end fixing portion 70. Then, the injection needle 24 becomes fitted in the base-side axial space 80. The injection needle 24 fitted in the base-side axial space 80 gets caught on the hook portion 68. If a vibration caused when the hook portion 68 hooks the tip end portion of the injection needle 24 is transmitted to the user's hand, the user stops pushing the moment receiving portion 44. At this time, the injection-needle cover 30 protects the injection needle 24 as shown in FIG. 2. If the injection-needle cover 30 protects the injection needle 24, the user disposes of the syringe 20 with the injection-needle cover 30 on it.

[Description of Effects of Injection-Needle Cover 30 According to the Embodiment]

In the embodiment, the injection-needle cover 30 in the folded state is attached to the syringe 20 in advance. The injection-needle cover 30 is fixed by the base portion 32 to a face of the syringe 20 from which the injection needle 24 is protruding. At this time, the injection needle 24 passes through the intra-cylinder space 82. The injection-needle cover 30 is extended by sliding the injection needle contact portion 66 along a side face of the injection needle 24. As the injection needle contact portion 66 slides along the side face of the injection needle 24, the portion of the injection needle 24 connected to the cylinder 22 is housed in the space formed by the connected portion fitting space forming portion 36. The injection needle 24 passing through the intra-cylinder space 82 gradually becomes fitted in the base-side axial space 80 and the tip-end-side axial space 84. The injection needle 24 passes through the intra-cylinder space 82 when the injection needle 24 becomes fitted in the base-side axial space 80 and the tip-end-side axial space 84. This is because the base-side axial space 80 communicates with the intra-cylinder space 82, the intra-cylinder space 82 communicates with the tip-end-side axial space 84, the base-side axial space 80 and the tip-end-side axial space 84 are aligned with each other, and the paired tip-end-side wall portions 64 are disposed on the opposite side of the cylinder portion 62 from the paired base-side wall portions 60. Before the injection needle contact portion 66 starts to slide on the side face of the injection needle 24, the base hinges 34 open. When the base hinges 34 open, the connected portion fitting space forming portion 36 turns. When the connected portion fitting space forming portion 36 turns, the injection needle enclosure portion 40 turns as well. This is because the injection needle enclosure portion 40 is connected to the connected portion fitting space forming portion 36 by the connecting hinges 38. When the injection needle enclosure portion 40 turns, the injection needle contact portion 66 comes in contact with the side face of the injection needle 24. Unless the connecting hinges 38 open insufficiently, a portion of the force receiving portion 100 which faces the injection needle 24 after the injection needle 24 becomes fitted in the base-side axial space 80 and the tip-end-side axial space 84 (i.e., injection needle facing portion 110) and an area on a side of the portion close to the tip-end-side axial space 84 come in direct contact with the side face of the injection needle 24 in many cases. If the connecting hinges 38 open insufficiently, the bottom curved face 140 rather than the injection needle facing portion 110 and the easy sliding portion 112 is likely to come in direct contact with the side face of the injection needle 24 as shown in FIG. 11 when the injection needle contact portion 66 starts to slide on the side face of the injection needle 24. In either case, the base hinges 34 open more than the connecting hinges 38 when the injection needle contact portion 66 starts to slide on the side face of the injection needle 24. Because the base hinges 34 open, the injection needle enclosure portion 40 turns. As a result, the injection needle contact portion 66 comes in contact with the side face of the injection needle 24. Because the force receiving portion 100 has the easy sliding portion 112 and the easy sliding portion 112 is disposed in an area adjacent to the injection needle, the force receiving portion 100 slides more easily when the injection needle contact portion 66 starts to slide on the side face of the injection needle 24 than the case where the edge 114 having the equal coefficient of static friction to a surface of the connecting portion 102 and crossing the injection needle 24 slides along the injection needle 24. Because the force receiving portion 100 slides easily, the injection-needle cover 30 is likely to be extended smoothly.

When the injection needle contact portion 66 slides on the side face of the injection needle 24, the connecting hinges 38 open. The injection needle contact zone 120 is extending along the direction of the movement of the easy sliding portion 112 in the opening of the connecting hinges 38. Because the injection needle contact zone 120 is a zone provided to the easy sliding portion 112, the easy sliding portion 112 slides on the side face of the injection needle 24 as the connecting hinges 38 open when the injection needle contact portion 66 slides on the side face of the injection needle 24. In this way, as compared with the case in which the injection needle contact zone 120 is not extending along the direction of the movement of the easy sliding portion 112 in the opening of the connecting hinges 38, it is possible to extend the injection-needle cover 30 smoothly for a longer time.

If the curved face is provided from one end to the other end of the injection needle contact zone 120, as compared with the case in which a plurality of flat faces are arranged in a row, for example, in the injection needle contact zone 120, the injection needle contact zone 120 smoothly slides on the side face of the injection needle 24. If the injection needle contact zone 120 can slide smoothly, as compared with the case in which the injection needle contact zone 120 cannot slide smoothly, it is possible to extend the injection-needle cover 30 smoothly.

If the moment receiving portion 44 receives the moment, as compared with the case in which a portion of the injection-needle cover 30 other than the connected portion fitting space forming portion 36 receives moment (e.g., the case in which the moment is applied to the connected portion fitting space forming portion 36 via the connecting hinges 38 by pinching the tip-end-side wall portions 64 between a thumb and a finger and moving the tip-end-side wall portions 64 in the direction along the injection needle 24), direct contact of the area adjacent to the injection needle with the side face of the injection needle 24 is facilitated. Because the direct contact of the area adjacent to the injection needle with the side face of the injection needle 24 is facilitated, the injection-needle cover 30 is more likely to be extended smoothly as compared with the case in which the connected portion fitting space forming portion 36 does not have the moment receiving portion 44.

Depending on degrees of opening of the connecting hinges 38 when the base hinges 34 start to open, a portion of the bottom plate portion 130 from the opposite face from a face facing the base-side axial space 80 to an end portion facing the intra-cylinder space 82 may come in contact with the injection needle 24 earlier than the area adjacent to the injection needle in some cases. If this portion is provided with the bottom curved face 140, even if the portion comes in contact with the injection needle 24 earlier than the area adjacent to the injection needle, the portion can move smoothly after the contact.

Because the plate-shaped portion 132 bends when the force receiving portion 100 receives the force from the injection needle 24, the injection needle contact portion 66 is more likely to start to slide on the side face of the injection needle 24 than when the plate-shaped portion 132 does not bend. If the injection needle contact portion 66 is more likely to start to slide on the side face of the injection needle 24, the injection-needle cover 30 is move likely to be extended smoothly than when the injection needle contact portion 66 is less likely to start to slide.

By increasing a difference between a thickness and a width of the plate-shaped portion 132, it is possible to easily increase a difference between bendability of the plate-shaped portion 132 in the direction from the tip-end-side axial space 84 toward the base-side axial space 80 and bendability of the plate-shaped portion 132 in the direction orthogonal to the direction. By increasing the difference in bendability, the plate-shaped portion 132 becomes more likely to bend in the direction from the tip-end-side axial space 84 toward the base-side axial space 80. As a result, the injection-needle cover 30 becomes more likely to be extended smoothly.

Because the plate-shaped portion 132 faces one of the paired base-side wall portions 60 with the clearance 160 left therebetween, a portion where the clearance 160 is provided bends easily. If the force receiving portion 100 similarly has the clearance 160, the plate-shaped portion 132 becomes more likely to bend in the direction from the tip-end-side axial space 84 toward the base-side axial space 80 than when the force receiving portion 100 does not have the clearance 160. As a result, the injection-needle cover 30 becomes more likely to be extended smoothly.

If the injection needle enclosure portion 40 further has the hook portion 68, the injection needle 24 which has become fitted in the base-side axial space 80 and the tip-end-side axial space 84 is less likely to be detached than when the injection needle enclosure portion 40 does not have the hook portion 68. Moreover, if the plate-shaped portion 132 is connected to the base-side wall portion 60 toward which the detachment preventing portion 152 is protruding, faces the different base-side wall portion 60 from the base-side wall portion 60, toward which the detachment preventing portion 152 is protruding, with the clearance 160 left therebetween, and the inclined face 154 is disposed from the tip end portion of the columnar portion 150 to the tip end portion of the detachment preventing portion 152, the injection needle 24 is less likely to become fitted in the clearance 160 than when such a hook portion 68 does not exist. If the injection needle 24 is less likely to become fitted in the clearance 160, the injection needle 24 is less likely to be covered with the injection-needle cover 30. If the injection needle enclosure portion 40 further has the needle tip end fixing portion 70, the injection needle 24 which has become fitted in the base-side axial space 80 and the tip-end-side axial space 84 is less likely to be detached than when the injection needle enclosure portion 40 does not have the needle tip end fixing portion 70.

[Description of Organoleptic Examination]

Figure 12:
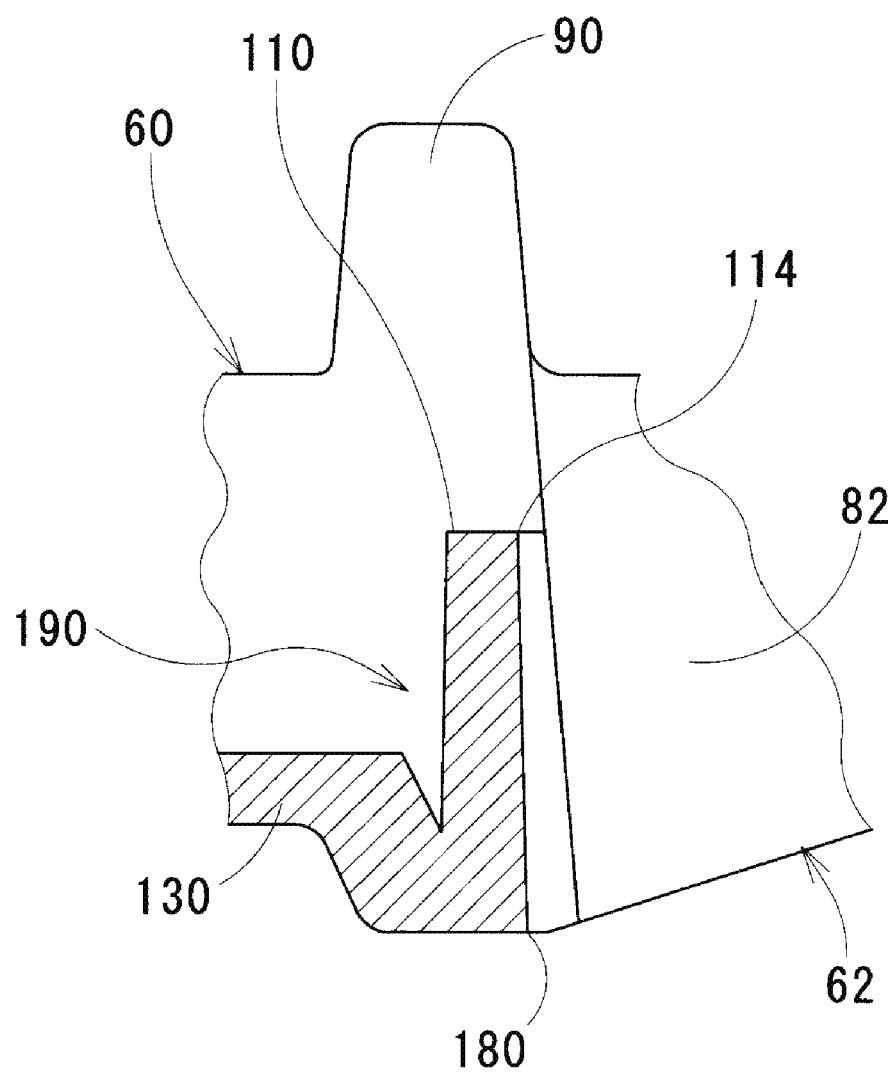
FIG. 12 is a sectional view of an injection needle contact portion of a comparative injection-needle cover.

The injection-needle cover 30 described by using FIGS. 1 to 11 (hereafter referred to as "the injection-needle cover according to the invention") and a comparative injection-needle cover described below were compared with each other in terms of operation. The comparative injection-needle cover has the same structure as the injection-needle cover according to the invention except the following points. The points are that the comparative injection-needle cover has an edge 114 instead of the easy sliding portion 112 of the injection-needle cover according to the invention and that the comparative injection-needle cover has a bottom edge 180 instead of the bottom curved face 140. FIG. 12 is a sectional view of an injection needle contact portion 190 of the comparative injection-needle cover.

An examiner prepared 1100 injection-needle covers according to the invention respectively attached to syringes as first-type samples. As second-type samples, the examiner prepared 1100 comparative injection-needle covers respectively attached to the same kind of syringes as the syringes of the first-type samples. As third-type samples, the examiner prepared 1100 injection-needle covers according to the invention respectively attached to other syringes with thick injection needles. As fourth-type samples, the examiner prepared 1100 comparative injection-needle covers respectively attached to the same kind of syringes as the syringes with the thick injection needles. On request from the examiner, 22 examinees evaluated smoothness of operation of each of the samples. Each of the examinees used 50 samples of each type.

Figure 13:
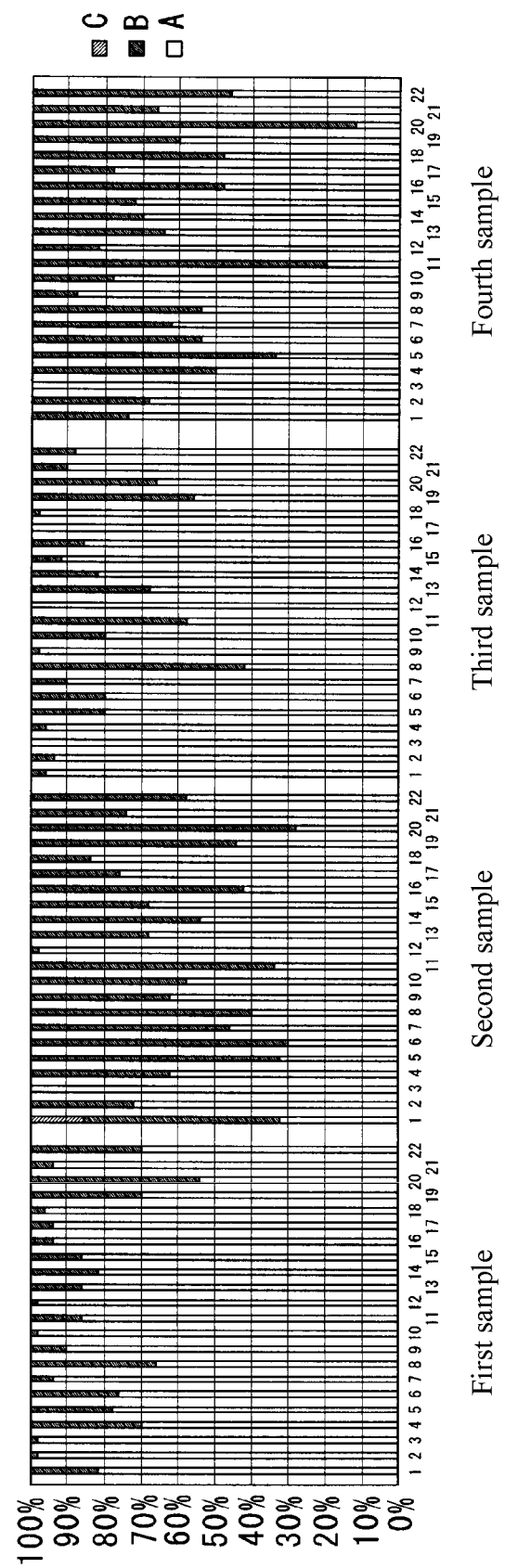
FIG. 13 is a diagram showing evaluation of the injection-needle covers according to the embodiment of the invention.

The smoothness of operation was rated on a three-point scale. If a cover operated very smoothly, the cover was rated as A. If a cover operated to the end while giving a scratchy feeling, the cover was rated as B. If a cover got caught firmly and stopped operating, the cover was rated as C. Results of the evaluation are shown in Table 1. Percentages of A, B, and C ratings given by the respective examinees are shown in FIG. 13. FIG. 13 shows the percentages of the ratings for each type of samples. Respective percentage bar charts in FIG. 13 show the percentages of the ratings by the respective examinees.

ratings for the second-type samples was 57.4%. A percentage of B ratings for the second-type samples was 42.0%. A percentage of C ratings for the second-type samples was 0.6%. A percentage of A ratings for the third-type samples was 83.6%. A percentage of B ratings for the third-type sample was 16.4%. A percentage of C ratings for the third-type samples was 0%. A percentage of A ratings for the fourth-type samples was 60.4%. A percentage of B ratings for the fourth-type samples was 39.6%. A percentage of C ratings for the fourth-type samples was 0%.

According to Table 1, the percentage of A ratings for the first-type samples is about 30% higher than the percentage of A ratings for the second-type samples. The percentage of A ratings for the third-type samples is about 20% higher than the percentage of A ratings for the fourth-type samples. From these results, it can be seen that the injection-needle cover according to the invention is much less likely to give a scratchy feeling than the comparative injection-needle cover.

[Description of Variations]

The embodiment disclosed this time is just one example in every respect. The scope of the invention is not restricted by the above-described embodiment. It is needless to say that the invention can be changed in various ways in design without departing from the gist of the invention.

Figure 14:
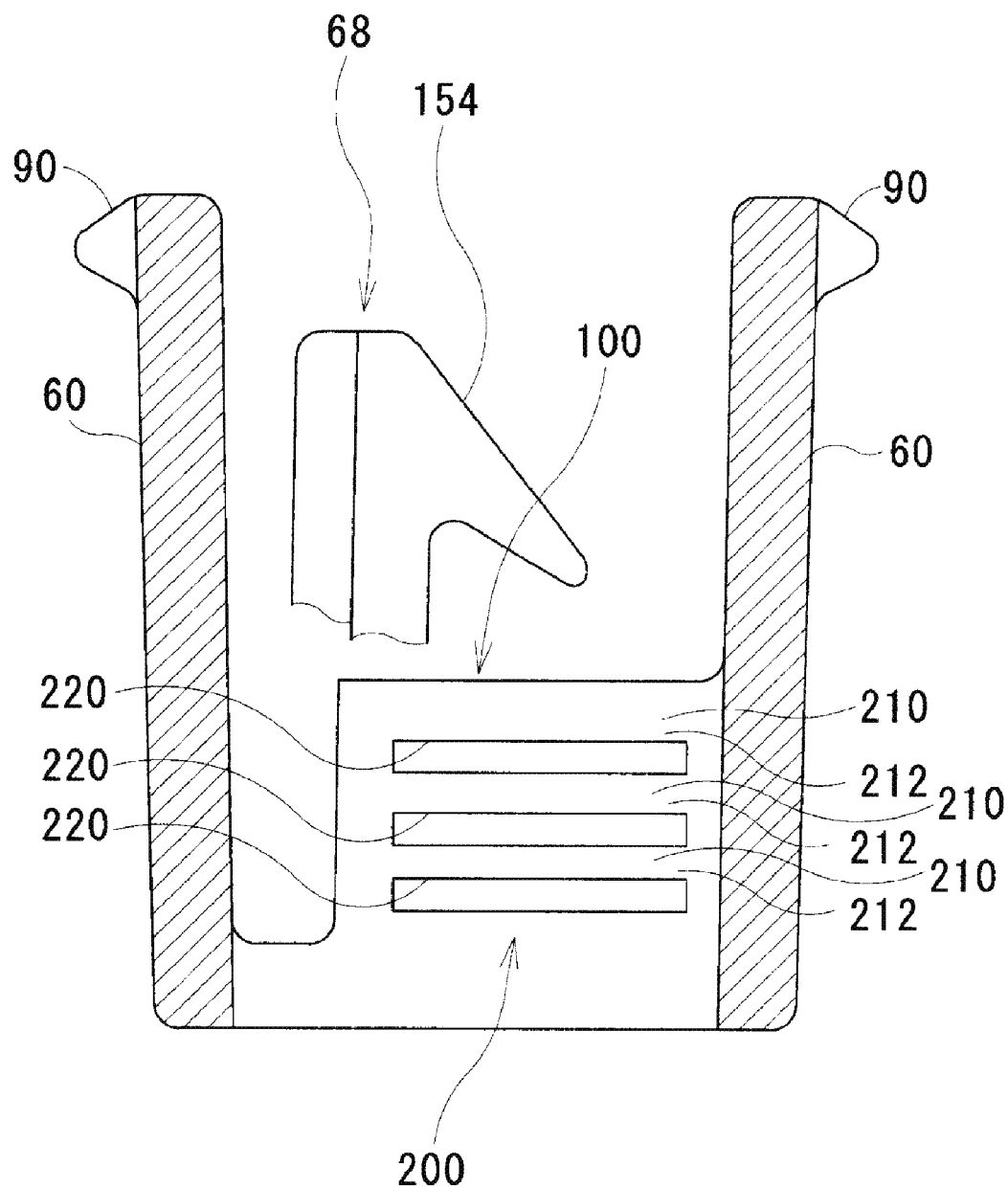
FIG. 14 is a view showing a flexible body portion according to a variation of the invention.

For example, the structure of the connecting portion 102 is not restricted to that described above. The connecting portion 102 may have a portion which is a kind of flexible body portion similarly to the plate-shaped portion but is not in a plate shape in place of the plate-shaped portion. Similarly to the plate-shaped portion, the flexible body portion bends more in a direction from a tip-end-side axial space 84 toward a base-side axial space 80 than in a direction orthogonal to the direction from the tip-end-side axial space 84 toward the base-side axial space 80 when a force receiving portion 100 receives a force from an injection needle 24. In this case, again, because the flexible body portion bends when the force receiving portion 100 receives the force from the injection needle 24, an injection needle contact portion 66 becomes more likely to start to slide on a side face of the injection needle 24 than when the flexible body portion does not bend. If the injection needle contact portion 66 is more likely to start to slide on the side face of the injection needle 24, an injection-needle cover 30 is more likely to be extended smoothly than when the injection needle contact portion 66 is less likely to start to slide. A specific structure of the flexible body portion is not especially restricted. For example, FIG. 14 shows an example of such a flexible body portion 200. The flexible body portion 200 may have less deformable portions 210 and more deformable portions 212.

TABLE 1

|  | First type Injection-needle cover according to the invention (22 examinees × 50 covers/examinee) | Second type Comparative injection-needle cover (22 examinees × 50 covers/examinee) | Third type Injection-needle cover according to the invention (22 examinees × 50 covers/examinee) | Fourth type Comparative injection-needle cover (22 examinees × 50 covers/examinee) |
| --- | --- | --- | --- | --- |
| A rating | 84.5% | 57.4% | 83.6% | 60.4% |
| B rating | 15.5% | 42.0% | 16.4% | 39.6% |
| C rating | 0.0% | 0.6% | 0.0% | 0.0% |

As is clear from Table 1, a percentage of A ratings for the first-type samples was 84.5%. A percentage of B ratings for the first-type samples was 15.5%. A percentage of C ratings for the first-type samples was 0.0%. A percentage of A The less deformable portions 210 are extending in directions crossing base-side wall portions 60. The more deformable portions 212 are extending along the less deformable portions 210 and more likely to be deformed than the less deformable portions 210. The more deformable portions 212 may be provided with slits 220. Moreover, the slits 220 are extending along the less deformable portions 210. In this case, if the less deformable portions 210 and the more deformable portions 212 are extending in the directions crossing the base-side wall portions 60, the flexible body portion 200 is more likely to be deformed in a direction from a tip-end-side axial space 84 toward a base-side axial space 80 than when flexible body portion 200 has uniform deformability throughout itself or when less deformable portions 210 and more deformable portions 212 are extending in directions along base-side wall portions 60. Furthermore, bending in a direction orthogonal to the direction is suppressed. Because the flexible body portion 200 is likely to be deformed in the direction from the tip-end-side axial space 84 toward the base-side axial space 80 and the bending of the flexible body portion 200 in the direction orthogonal to the direction is suppressed, the flexible body portion 200 is less likely to deform an injection needle when an injection needle contact portion 66 slides on a side face of the injection needle 24. Moreover, by providing the slits 220 to the more deformable portions 212, it is possible to reduce an amount of material for manufacture. Besides the flexible body portion shown in FIG. 14, it is also possible to employ a flexible body portion having slits (and less deformable portions 210 and more deformable portions 212) extending in directions different from those shown in FIG. 14 or a flexible body portion having circular holes instead of slits. The connecting portion 102 may have a portion which is a kind of structural body portion similarly to the flexible body portion and which is different from the flexible body portion in place of the flexible body portion. The structural body portion is protruding from an end portion of a bottom plate portion 130 facing an intra-cylinder space 82 (the end portion provided with a bottom curved face 140) toward a base-side axial space 80. A specific structure of the structural body portion is not especially restricted.

A form of the easy sliding portion 112 is not restricted to the form described above. For example, an easy sliding portion 112 may be a porous structure which can contain lubricant. An easy sliding portion 112 may have a flat face which comes in contact with an injection needle 24.

The position of the injection needle contact portion 66 is not restricted to the position described above. For example, an injection needle contact portion 66 may be disposed in an intra-cylinder space 82. In this case, a connecting portion 102 may connect a cylinder portion 62 and a force receiving portion 100. A form of the injection needle contact portion 66 is not especially restricted. For example, different portions of an injection needle contact portion 66 may have different thicknesses.

In this paragraph, an invention different from the present invention will be mentioned. In the invention described in this paragraph, it is essential only that a connecting portion have a flexible body portion and a force receiving portion may not have an easy sliding portion. In this case, if the connecting portion has the flexible body portion, the injection-needle cover 30 becomes more likely to be extended smoothly. In other respects, the invention described in this paragraph is similar to the present invention, i.e., the invention described in paragraphs earlier than this paragraph.

DESCRIPTION OF REFERENCE SIGNS

20: Syringe
22: Cylinder
24: Injection needle
26: Cylindrical cover
28: Injection needle protruding face
30: Injection-needle cover
32: Base portion
34: Base hinge
36: Connected portion fitting space forming portion
38: Connecting hinge
40: Injection needle enclosure portion
42: Retaining portion
44: Moment receiving portion
46: Arm portion
48: Rib
50: Central axis
52: Base axis
54: Connection axis
60: Base-side wall portion
62: Cylinder portion
64: Tip-end-side wall portion
66: Injection needle contact portion
68: Hook portion
70: Needle tip end fixing portion
80: Base-side axial space
82: Intra-cylinder space
84: Tip-end-side axial space
90: Fixing lug
100: Force receiving portion
102: Connecting portion
110: Injection needle facing portion
112: Easy sliding portion
114: Edge
120: Injection needle contact zone
122: Injection needle position correcting zone
130: Bottom plate portion
132: Plate-shaped portion
140: Bottom curved face
150: Columnar portion
152: Detachment preventing portion
154: Inclined face
160: Clearance
170: Thumb
180: Bottom edge
190: Injection needle contact portion
210: Less deformable portion
212: More deformable portion
220: Slit

The invention claimed is:

1. An injection-needle cover comprising:
a base portion that is fixed to an injection needle protruding face of a syringe, having a cylinder and an injection needle protruding from the cylinder, so as to enclose the injection needle, the injection needle protruding face being a face of the syringe from which the injection needle is protruding from the cylinder;
a base hinge, which is a hinge provided to the base portion;
a connected portion fitting space forming portion, which is connected to the base portion by the base hinge so as to turn about a base axis orthogonal to a central axis of the injection needle and which forms a space where a portion of the injection needle connected to the cylinder is to become fitted;
a connecting hinge, which is a hinge provided to the connected portion fitting space forming portion; and
an injection needle enclosure portion, which is connected to the connected portion fitting space forming portion by the connecting hinge so as to turn about a connection axis parallel to the base axis, the injection needle enclosure portion including:

paired base-side wall portions forming a base-side axial space where a portion of the injection needle is to become fitted, a cylinder portion, which is continuous from the paired base-side wall portions and which forms an intra-cylinder space communicating with the base-side axial space, paired tip-end-side wall portions that are continuous from the cylinder portion, form a tip-end-side axial space where a tip end portion of the injection needle is to become fitted so that the tip-end-side axial space communicates with the intra-cylinder space, and that are disposed on the opposite side of the cylinder portion from the paired base-side wall portions so that the base-side axial space and the tip-end-side axial space are aligned with each other, and an injection needle contact portion disposed at such a position in one of the base-side axial space and the intra-cylinder space as to come in contact with the injection needle when the base hinge opens, wherein the injection needle contact portion has:
a force receiving portion that is disposed between the base-side wall portions and receives a force from the injection needle when the force receiving portion comes in contact with the injection needle, and
a connecting portion that connects the paired base-side wall portions or the cylinder portion to the force receiving portion;

wherein the force receiving portion has an easy sliding portion that is disposed in an area adjacent to an injection needle and slides along the injection needle more easily as compared to an edge, which has an equal coefficient of static friction to a surface of the connecting portion and crossing the injection needle, slides along the injection needle, the area being closer to an area on a side of the tip-end-side axial space than a portion, that faces the injection needle after the injection needle becomes fitted in the base-side axial space and the tip-end-side axial space;

wherein the easy sliding portion has an injection needle contact zone extending along a direction of movement of the easy sliding portion in opening of the connecting hinge;

wherein the injection needle contact zone is provided with a curved face extending from one end to the other end of the injection needle contact zone in the direction of the movement of the easy sliding portion in the opening of the connecting hinge;

wherein the connecting portion has:
a bottom plate portion that is disposed in the base-side axial space to be adjacent to a boundary between the base-side axial space and the intra-cylinder space and opposite ends of which are connected to the base-side wall portions,
a structural body portion protruding from an end portion of the bottom plate portion facing the intra-cylinder space toward the base-side axial space,
a curved face is provided to a portion of the bottom plate portion extending from the opposite face from a face facing the base-side axial space to the end portion, and
a flexible body portion that bends more in a direction from the tip-end-side axial space toward the base-side axial space than in a direction orthogonal to the direction from the tip-end-side axial space toward the base-side axial space when the force receiving portion receives the force from the injection needle, and wherein the flexible body portion has a plate-shaped portion disposed to be orthogonal to a bending direction, which is the direction from the tip-end-side axial space toward the base-side axial space, wherein the plate-shaped portion faces one of the paired base-side wall portions with a clearance left therebetween, and the force receiving portion faces the one of the paired base-side wall portions, which the plate-shaped portion faces with the clearance left therebetween, with a clearance left therebetween.

2. The injection-needle cover according to claim 1, wherein the connected portion fitting space forming portion has a moment receiving portion for receiving moment about the base axis as a turning center.

3. The injection-needle cover according to claim 1, wherein the injection needle enclosure portion further has a hook portion that protrudes into the base-side axial space and hooks the injection needle when the injection needle becomes fitted in the base-side axial space and the tip-end-side axial space, the hook portion has:
a columnar portion disposed along the paired base-side wall portions in the base-side axial space,
a detachment preventing portion protruding from the columnar portion toward one of the paired base-side wall portions, and
an inclined face disposed from a tip end portion of the columnar portion to a tip end portion of the detachment preventing portion and inclined with respect to a direction along the paired base-side wall portions, wherein the plate-shaped portion is connected to the base-side wall portion, toward which the detachment preventing portion is protruding, and faces the different base-side wall portion from the base-side wall portion, toward which the detachment preventing portion is protruding, with the clearance left therebetween.

4. The injection-needle cover according to claim 3, wherein the flexible body portion has
a less deformable portion extending in a direction crossing the base-side wall portions and
a more deformable portion extending along the less deformable portion and being relatively more deformable than the less deformable portion.

5. The injection-needle cover according to claim 4, wherein the more deformable portion is provided with a slit extending along the less deformable portion.

6. The injection-needle cover according to claim 3, wherein the connected portion fitting space forming portion has a moment receiving portion for receiving moment about the base axis as a turning center.

7. The injection-needle cover according to claim 1, wherein the flexible body portion has
a less deformable portion extending in a direction crossing the base-side wall portions, and
a more deformable portion extending along the less deformable portion and being relatively more deformable than the less deformable portion.

8. The injection-needle cover according to claim 7, wherein the more deformable portion is provided with a slit extending along the less deformable portion.

* * * * *